United States Patent [19]
Hunt

[11] Patent Number: 5,965,732
[45] Date of Patent: Oct. 12, 1999

[54] SULFONAMIDE ENDOTHELIN ANTAGONISTS

[75] Inventor: John T. Hunt, Princeton, N.J.

[73] Assignee: Bristol-Myers Squibb Co., Princeton, N.J.

[21] Appl. No.: 08/114,251

[22] Filed: Aug. 30, 1993

[51] Int. Cl.$^6$ .................................................. C07D 237/20
[52] U.S. Cl. ...................... 544/224; 544/239; 544/240; 544/241
[58] Field of Search .................. 544/224, 239, 544/240, 241

[56] References Cited

U.S. PATENT DOCUMENTS

| | | | |
|---|---|---|---|
| 2,524,802 | 10/1950 | Hultquist et al. ........................ | 544/224 |
| 2,542,856 | 2/1951 | Wright et al. ............................. | 544/224 |
| 2,888,455 | 5/1959 | Kano et al. ............................... | 548/246 |
| 3,055,886 | 9/1962 | Goodemoot et al. .................... | 544/224 |
| 4,415,496 | 11/1983 | Harris et al. .............................. | 540/521 |
| 4,661,479 | 4/1987 | Wyvratt, Jr. et al. .................... | 514/214 |
| 5,464,853 | 11/1995 | Chan et al. ................................ | 514/378 |
| 5,514,691 | 5/1996 | Chan et al. . | |
| 5,514,696 | 5/1996 | Murugesan et al. . | |
| 5,571,821 | 11/1996 | Chan et al. ............................... | 514/312 |

FOREIGN PATENT DOCUMENTS

| | | |
|---|---|---|
| 29589/92 | 5/1993 | Australia . |
| 76072 | 4/1983 | European Pat. Off. . |
| 194548 | 9/1986 | European Pat. Off. . |
| 404525 | 12/1990 | European Pat. Off. . |
| 443983 | 8/1991 | European Pat. Off. . |
| 510526 | 10/1992 | European Pat. Off. . |
| 526708 | 2/1993 | European Pat. Off. . |
| 0558258 | 9/1993 | European Pat. Off. . |
| 0569193 | 11/1993 | European Pat. Off. . |
| 804036 | 11/1958 | United Kingdom . |
| 1473433 | 5/1977 | United Kingdom . |
| 2228933 | 9/1990 | United Kingdom . |
| 93/08799 | 5/1993 | WIPO . |
| 95/26957 | 10/1995 | WIPO . |

OTHER PUBLICATIONS

Stein, P.D. et al., The Discovery of Sulfonamide Endothelin Antagonists and the Development of the Orally Active ET(A) Antagonist 5–(dimethylamino)–N–(3, 4–dimethyl–5–isoxazolyl)–1–naphthalenesulfonamide, *J. of Medicinal Chemistry*, vol. 37, No. 3 (1994) pp. 329–331.

Chan, M.F. et al., Identification of a New Class of ET(A) Selective Endothelin Antagonists by Pharmacophore Directed Screening, *Biochemical and Biophysical Research Comm.*, vol. 201, No. 1 (1994) pp.228–234.

Heinisch, G. et al., Pharmacologically Active Pyridazine Derivatives. Part 1, *Progress In Medicinal Chemistry*, vol. 27 (1990) pp. 2–49.

Kruger, T. E. et al., Die Antibakterielle Wirkung Des Nicht Eiweissgebundenen Anteils Der Sulfanilamide Im Menschlichen Plasmawasser, *Arzneimittel–Forschung*, vol. 15, No. 11, (1965) pp. 1390–1317.

Doherty, A.M., Endothelin: A New Challenge, *J. of Medicinal Chemistry*, vol. 35, No. 9 (1992) pp. 1493–1508.

Becker et al, *Chemical Abstracts*, vol. 75, No. 49119 (1971).

Naito et al, *Chemical Abstracts*, vol. 68, No. 114622 (1968).

Mihara et al, *European Journal of Pharmacology*, 246, pp. 33–38, 1993.

Clozel et al, *Nature*, 365, pp. 759–761 (1993).

Derwent Abstract No. 88–289069/41 Feb. 27, 1987 (Abstract for JP63/211271).

Derwent Abstract No. 88–195835/28 Nov. 26, 1986 (Abstract for JP63/135368).

Derwent Abstract No. 88–061295/09 Jul. 9, 1986 (Abstract for JP63/017870).

Derwent Abstract No. 87–152485/22 Oct. 11, 1985 (Abstract for JP62/087581).

Derwent Abstract No. 62299 E/30 Dec. 11, 1980 (Abstract for JP57/098253).

Derwent Abstract No. 40927 D/23 Sep. 11, 1979 (Abstract for JP56/040660).

Derwent Abstract No. 91–254550/35 Feb. 19, 1990 (Abstract for EP 443983).

Derwent Abstract No. 86–246709/38 Nov. 27, 1985 (Abstract for EP 194548).

Derwent Abstract No. 35012 K/15 Sep. 24, 1981 (Abstract for EP 76072).

Allen et al., "Preparation . . . antagonists", CA116(11):106284Z, p. 778, 1992.

R.D. Desai et al., *Chemical Abstracts*, vol. 71, No. 11, (1969) 49825c.

R.D. Desai et al., *Chemical Abstracts*, vol. 71, No. 3, (1969) 12872q.

S. Norio et al., *Chemical Abstracts*, vol. 70, No. 19, (1969) 87639g.

T. Saito, *Chemical Abstracts*, vol. 73, No. 23, (1970) 120511w.

*Primary Examiner*—Emily Bernhardt
*Attorney, Agent, or Firm*—John M. Kilcoyne; Suzanne E. Babajko; Ronald S. Hermenau

[57] ABSTRACT

Compounds of the formula

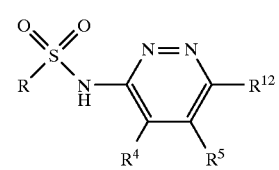

inhibit endothelin, wherein:

R is phenyl, naphthyl or biphenyl, each of which may be substituted.

14 Claims, No Drawings

SULFONAMIDE ENDOTHELIN ANTAGONISTS

FIELD OF THE INVENTION

This invention relates to endothelin antagonists useful, inter alia, for treatment of hypertension.

BRIEF DESCRIPTION OF THE INVENTION

Compounds of the formula

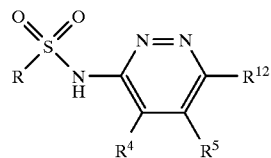

I and pharmaceutically acceptable salts thereof are endothelin receptor antagonists useful, inter alia, as antihypertensive agents. Throughout this specification, the above symbols are defined as follows:

R is phenyl, naphthyl or biphenyl, each of which may be substituted with $R^1$, $R^2$ and $R^3$;

$R^1$, $R^2$ and $R^3$ are each independently
 (a) hydrogen;
 (b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$;
 (c) halo;
 (d) hydroxyl;
 (e) cyano;
 (f) nitro;
 (g) —C(O)H or —C(O)$R^6$;
 (h) —CO$_2$H or —CO$_2R^6$;
 (i) —SH, —S(O)$_nR^6$, —S(O)$_m$—OH, —S(O)$_m$—OR$^6$, —O—S(O)$_m$—R$^6$, —O—S(O)$_m$OH or —O—S(O)$_m$—OR$^6$;
 (j) —$Z^4$—NR$^7$R$^8$; or
 (k) —$Z^4$—N(R$^{11}$)—$Z^5$—NR$^9$R$^{10}$;

$R^4$, $R^5$ and $R^{12}$ are each independently
 (a) hydrogen;
 (b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$;
 (c) halo;
 (d) hydroxyl;
 (e) cyano;
 (f) nitro;
 (g) —C(O)H or —C(O)$R^6$;
 (h) —CO$_2$H or —CO$_2R^6$;
 (i) —SH, —S(O)$_nR^6$, —S(O)$_m$—OH, —S(O)$_m$—OR$^6$, —O—S(O)$_m$—R$^6$, —O—S(O)$_m$OH or —O—S(O)$_m$—OR$^6$;
 (j) —$Z^4$—NR$^7$R$^8$;
 (k) —$Z^4$—N(R$^{11}$)—$Z^5$—NR$^9$R$^{10}$; or
 (l) $R^4$ and $R^5$, or $R^5$ and $R^{12}$ together are alkylene or alkenylene (either of which may be substituted with $Z^1$, $Z^2$ and $Z^3$), completing a 4- to 8-membered saturated, unsaturated or aromatic ring together with the carbon atoms to which they are attached;

provided that when R is phenyl, at least two of $R^4$, $R^5$ and $R^{12}$ are other than hydrogen;

$R^6$ is alkyl, alkenyl, alkynyl, alkoxy, cycloalkyl, cycloalkylalkyl, cycloalkenyl, cycloalkenylalkyl, aryl or aralkyl, any of which may be substituted with $Z^1$, $Z^2$ and $Z^3$;

$R^7$ is
 (a) hydrogen;
 (b) alkyl, alkenyl, alkynyl, alkoxy, cycloalkyl, cycloalkylalkyl, cycloalkenyl, cycloalkenylalkyl, aryl or aralkyl, any of which may be substituted with $Z^1$, $Z^2$ and $Z^3$;
 (c) cyano;
 (d) hydroxyl;
 (e) —C(O)H or —C(O)$R^6$;
 (f) —CO$_2R^6$; or
 (g) —SH, —S(O)$_nR^6$, —S(O)$_m$—OR$^6$, —O—S(O)$_m$—R$^6$ or —O—S(O)$_m$—OR$^6$, except when $Z^4$ is —S(O)$_n$—;

$R^8$ is
 (a) hydrogen;
 (b) —C(O)H or —C(O)$R^6$, except when $Z^4$ is —C(O)— and $R^7$ is —C(O)H, —C(O)$R^6$ or —CO$_2R^6$; or
 (c) alkyl, alkenyl, alkynyl, alkoxy, cycloalkyl, cycloalkylalkyl, cycloalkenyl, cycloalkenylalkyl, aryl or aralkyl, any of which may be substituted with $Z^1$, $Z^2$ and $Z^3$; or $R^7$ and $R^8$ together are alkylene or alkenylene (either of which may be substituted with $Z^1$, $Z^2$ and $Z^3$), completing a 3- to 8-membered saturated, unsaturated or aromatic ring together with the nitrogen atom to which they are attached;

$R^9$ is
 (a) hydrogen;
 (b) hydroxyl;
 (c) —C(O)H or —C(O)$R^6$;
 (d) —CO$_2R^6$;
 (e) —SH, —S(O)$_nR^6$, —S(O)$_m$—OR$^6$, —O—S(O)$_m$—R$^6$ or —O—S(O)$_m$—OR$^6$; or
 (f) alkyl, alkenyl, alkynyl, alkoxy, cycloalkyl, cycloalkylalkyl, cycloalkenyl, cycloalkenylalkyl, aryl or aralkyl, any of which may be substituted with $Z^1$, $Z^2$ and $Z^3$;

$R^{10}$ is
 (a) hydrogen;
 (b) —C(O)H or —C(O)$R^6$, except when $Z^5$ is —C(O)— and $R^9$ is —C(O)H, —C(O)$R^6$ or —CO$_2R^6$; or
 (c) alkyl, alkenyl, alkynyl, alkoxy, cycloalkyl, cycloalkylalkyl, cycloalkenyl, cycloalkenylalkyl, aryl or aralkyl, any of which may be substituted with $Z^1$, $Z^2$ and $Z^3$;

$R^{11}$ is
 (a) hydrogen;
 (b) hydroxyl or —CO$_2R^6$, except when one of $R^9$ and $R^{10}$ is hydroxyl or —CO$_2R^6$;
 (c) —C(O)H or —C(O)$R^6$; or
 (d) alkyl, alkenyl, alkynyl, alkoxy, cycloalkyl, cycloalkylalkyl, cycloalkenyl, cycloalkenylalkyl, aryl or aralkyl, any of which may be substituted with $Z^1$, $Z^2$ and $Z^3$;

or any two of $R^9$, $R^{10}$ and $R^{11}$ together are alkylene or alkenylene (either of which may be substituted with $Z^1$, $Z^2$ and $Z^3$), completing a 3- to 8-membered saturated, unsaturated or aromatic ring together with the atoms to which they are attached;

$Z^1$, $Z^2$ and $Z^3$ are each independently (a) hydrogen;
(b) halo;
(c) hydroxy;
(d) alkyl, alkenyl, aralkyl, alkoxy, aryloxy or aralkoxy;
(e) —SH, —S(O)$_n$Z$^6$, S(O)$_m$—OH, —S(O)$_m$—OZ$^6$, —O—S(O)$_m$—Z$^6$, —O—S(O)$_m$OH or —O—S(O)$_m$—OZ$^6$;
(f) oxo;
(g) nitro;
(h) cyano;
(i) —C(O)H or —C(O)Z$^6$;
(j) —CO$_2$H or —CO$_2$Z$^6$; or
(k) —Z$^4$—NZ$^7$Z$^8$, —Z$^4$—N(Z$^{11}$)—Z$^5$Z$^6$ or —Z$^4$—N(Z$^{11}$)—Z$^5$—NZ$^7$Z$^8$;

Z$^4$ and Z$^5$ are each independently
(a) a single bond;
(b) —Z$^9$—S(O)$_m$—Z$^{10}$;
(c) —Z$^9$—C(O)—Z$^{10}$;
(d) —Z$^9$—C(S)—Z$^{10}$;
(e) —Z$^9$—O—Z$^{10}$;
(f) —Z$^9$—S—Z$^{10}$;
(g) —Z$^9$—C(O)—Z$^{10}$; or
(h) alkyl, alkenyl, alkynyl, cycloalkyl, cycloalkylalkyl, cycloalkenyl, cycloalkenylalkyl, aryl or aralkyl, any of which may be substituted with Z$^1$, Z$^2$ and Z$^3$;

Z$^6$, Z$^7$ and Z$^8$ are each independently hydrogen, alkyl, alkenyl, alkynyl, cycloalkyl, cycloalkylalkyl, cycloalkenyl, cycloalkenylalkyl, aryl, or aralkyl, or Z$^7$ and Z$^8$ together are alkylene or alkenylene, completing a 3- to 8-membered saturated, unsaturated or aromatic ring together with the nitrogen atom to which they are attached;

Z$^9$ and Z$^{10}$ are each independently a single bond, alkylene, alkenylene or alkynylene, Z$^{11}$ is
(a) hydrogen;
(b) hydroxyl;
(c) —C(O)H, —C(O)Z$^6$ or —CO$_2$Z$^6$, provided that when Z$^{11}$ is —CO$_2$Z$^6$, Z$^6$ is other than hydrogen; or
(d) alkyl, alkenyl, alkynyl, alkoxy, cycloalkyl, cycloalkylalkyl, cycloalkenyl, cycloalkenylalkyl, aryl or aralkyl;

or any two of Z$^7$, Z$^8$ and Z$^{11}$ together are alkylene or alkenylene, completing a 3- to 8-membered saturated, unsaturated or aromatic ring together with the atoms to which they are attached;

m is 1 or 2; and
n is 0, 1 or 2.

For compound 1, when R is

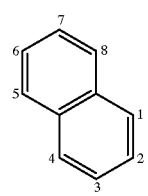

it is preferred that the sulfonamide is attached at position 1 or 2 and one of R$^1$, R$^2$ and R$^3$ is attached at position 5 or 6;

one of R$^1$, R$^2$ and R$^3$ is —NR$^7$R$^8$;

R$^4$, R$^5$ and R$^{12}$ are independently hydrogen, alkyl or halo; and

R$^7$ and R$^8$ are each independently hydrogen, alkyl, or —C(O)R$^6$ wherein R$^6$ is alkyl.

Most preferred of these compounds are those wherein one of R$^1$, R$^2$ and R$^3$ is —NR$^7$R$^8$ and the other two are hydrogen, —NR$^7$R$^8$ is attached at position 5 and the sulfonamide is attached at position 1, R$^4$ and R$^5$ are independently hydrogen or methyl, R$^{12}$ is halo and R$^7$ and R$^8$ are hydrogen, methyl, methylethyl, or acetyl.

For compound I, when R is biphenyl, it is preferred that one of R$^1$, R$^2$ and R$^3$ is 4'-alkyl or 4'-branched alkyl.

DETAILED DESCRIPTION OF THE INVENTION

Listed below are definitions of terms used in this specification. These definitions apply to the terms as used throughout this specification, individually or as part of another group, unless otherwise limited in specific instances.

The terms "alkyl" and "alkoxy" refer to straight or branched chain hydrocarbon groups having 1 to 10 carbon atoms. The terms "lower alkyl" and "lower alkoxy" refer to groups of 1 to 4 carbon atoms, which are preferred.

The term "aryl" or "ar-" refers to phenyl, naphthyl, and biphenyl.

The term "alkenyl" refers to straight or branched chain hydrocarbon groups of 2 to 10 carbon atoms having at least one double bond. Groups of two to four carbon atoms are preferred.

The term "alkynyl" refers to straight or branched chain groups of 2 to 10 carbon atoms having at least one triple bond. Groups of two to four carbon atoms are preferred.

The term "alkylene" refers to a straight chain bridge of 1 to 5 carbon atoms connected by single bonds (e.g., —(CH$_2$)$_m$— wherein m is 1 to 5), which may be substituted with 1 to 3 lower alkyl groups.

The term "alkenylene" refers to a straight chain bridge of 2 to 5 carbon atoms having one or two double bonds that is connected by single bonds (e.g., —CH=CH$_1$—CH=CH—, —CH$_2$—CH=CH—, —CH$_2$—CH=CH—CH$_2$—, —C(CH$_3$)$_2$CH=CH— and —CH(C$_2$H$_5$)—CH=CH—) which may be substituted with 1 to 3 lower alkyl groups.

The term "alkynylene" refers to a straight chain bridge of 2 to 5 carbon atoms that has a triple bond therein, is connected by single bonds, and may be substituted with 1 to 3 lower alkyl groups. Exemplary akynylene groups are —C≡C—, —CH$_2$—C≡C—, —CH(CH$_3$)—C≡C— and —C≡C—CH(C$_2$H$_5$)CH$_2$—.

The term "alkanoyl" refers to groups of the formula —C(O)alkyl.

The terms "cycloalkyl" and "cycloalkenyl" refers to cyclic hydrocarbon groups of 3 to 8 carbon atoms.

The term "aralkyl" refers to an alkyl group substituted by one or more aryl groups.

The terms "halogen" and "halo" refers to fluorine, chlorine, bromine and iodine.

The compounds of formula I form salts which are also within the scope of this invention. Pharmaceutically acceptable (i.e., non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, benzathine, N-methyl-D-glucamide and hydrabamine and with amino acids such as arginine, lysine and the like. Such salts may be obtained by reacting compound I with the desired ion in a medium in which the salt precipitates or in an aqueous medium followed by lyophilization.

When the $R^1$ to $R^5$ or $R^{12}$ substituents comprise a basic moiety, such as amino or substituted amino, compound I may form salts with a variety of organic and inorganic acids. Such salts include those formed with hydrochloric acid, hydrogen bromide, methanesulfonic acid, sulfuric acid, acetic acid, maleic acid, benzenesulfonate, toluenesulfonate and various other sulfonates, nitrates, phosphates, borates, acetates, tartrates, maleates, citrates, succinates, benzoates, ascorbates, salicylates and the like. Such salts may be formed by reacting compound I in an equivalent amount of the acid in a medium in which the salt precipitates or in an aqueous medium followed by lyophilization.

In addition, when the $R^1$ to $R^5$ or $R^{12}$ substituents comprise a basic moiety such as amino, zwitterions ("inner salts") may be formed.

Certain of the $R^1$ to $R^5$ and $R^{12}$ substituents of compound I may contain asymmetric carbon atoms. Such compounds of formula I may exist, therefore, in enantiomeric and diasteromeric forms and in racemic mixtures thereof. All are within the scope of this invention.

The compounds of formula I are antagonists of ET-1, ET-2, and/or ET-3 and are useful in treatment of all endothelin-dependent disorders. They are thus useful as antihypertensive agents. By the administration of a composition having one (or a combination) of the compounds of this invention, the blood pressure of a hypertensive mammalian (e.g., human) host is reduced.

The compounds of the present invention are also useful in the treatment of disorders related to renal, glomerular and mesangial cell function, including chronic renal failure, glomerular injury, renal damage secondary to old age, nephrosclerosis (especially hypertensive nephrosclerosis), nephrotoxicity (including nephrotoxicity related to imaging and contrast agents) and the like. The compounds of this invention may also be useful in the treatment of disorders related to paracrine and endocrine function.

The compounds of the present invention are also useful in the treatment of endotoxemia or endotoxin shock.

The compounds of the present invention are also useful as anti-ischemic agents for the treatment of, for example, heart, renal and cerebral ischemia and the like.

In addition, the compounds of this invention may also be useful as anti-arrhythmic agents; anti-anginal agents; anti-fibrillatory agents; anti-asthmatic agents; therapy for myocardial infarction; therapy for peripheral vascular disease (e.g., Raynaud's disease); anti-atherosclerotic agents; treatment of cardiac hypertrophy (e.g., hypertrophic cardiomyopathy); treatment of pulmonary hypertension; additives to cardioplegic solutions for cardiopulmonary bypasses; adjuncts to thrombolytic therapy; treatment of central nervous system vascular disorders such as stroke, migraine, and subarachnoid hemorrhage; treatment of central nervous system behavioral disorders; treatment of gastrointestinal diseases such as ulcerative colitis and Crohn's disease; anti-diarrheal agents; regulation of cell growth and cell migration; treatment of benign prostatic hyperplasia; treatment of lipid disorders; treatment of restenosis; and treatment of hepatoxicity and sudden death.

The compounds of this invention can also be formulated in combination with endothelin converting enzyme (ECE) inhibitors, such as phosphoramidon; platelet activating factor (PAF) antagonists; angiotensin II (AII) receptor antagonists; renin inhibitors; angiotensin converting enzyme (ACE) inhibitors such as captopril, zofenopril, fosinopril, ceranapril, alacepril, enalapril, delapril, pentopril, quinapril, ramipril, lisinopril, and salts of such compounds; neutral endopeptidase (NEP) inhibitors; calcium channel blockers; potassium channel activators; beta-adrenergic agents; antiarrhythmic agents; diuretics, such as chlorothiazide, hydrochlorothiazide, flumethiazide, hydroflumethiazide, bendroflumethiazide, methylchlorothiazide, trichloromethiazide, polythiazide or benzothiazide as well as ethacrynic acid, tricrynafen, chlorthalidone, furosemide, musolimine, bumetanide, triamterene, amiloride and spironolactone and salts of such compounds; thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories). If formulated as a fixed dose, such combination products employ the compounds of this invention within the dosage range described below and the other pharmaceutically active agent within its approved dosage range. The compounds of this invention may also be formulated with or useful in conjunction with antifungal and immunosuppressive agents such as amphotericin B, cyclosporins and the like to counteract the glomerular contraction and nephrotoxicity secondary to such compounds. The compounds of this invention may also be used in conjunction with hemodialysis.

The compounds of the invention can be administered orally or parenterally to various mammalian species known to be subject to such maladies, e.g., humans, in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) in single or 2 to 4 divided daily doses.

The active substance can be utilized in a composition such as tablet, capsule, solution or suspension containing about 5 to about 500 mg per unit of dosage of a compound or mixture of compounds of formula I or in topical form for wound healing (0.01 to 5% by weight compound of formula I, 1 to 5 treatments per day). They may be compounded in conventional matter with a physiologically acceptable vehicle or carrier, excipient, binder, preservative, stabilizer, flavor, etc., or with a topical carrier such as Plastibase (mineral oil gelled with polyethylene) as called for by accepted pharmaceutical practice.

The compounds of the invention may also be administered topically to treat peripheral vascular diseases and as such may be formulated as a cream or ointment.

The compounds of formula I can also be formulated in compositions such as sterile solutions or suspensions for parenteral administration. About 0.1 to 500 milligrams of a compound of formula I is compounded with a physiologically acceptable vehicle, carrier, excipient, binder, preservative, stabilizer, etc., in a unit dosage form as called for by accepted pharmaceutical practice. The amount of active substance in these compositions or preparations is such that a suitable dosage in the range indicated is obtained.

The compounds of the present invention may be prepared as follows.

A sulfonamide $$R-SO_2NH_2 \qquad \text{II}$$

is coupled with

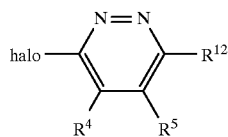

in an anhydrous organic solvent in the presence of a base (e.g., $Cs_2CO_3$) to form compound I.

The sulfonamide II may be prepared from $R-SO_2halo$ and $NH_3$.

Alternatively, the sulfonamide II wherein R is biphenyl substituted with $R^1$, $R^2$ and $R^3$ may be prepared by metal (e.g., palladium (0)) catalyzed coupling of the associated halo compound

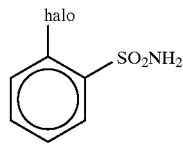

with aryl metalloids (i.e., aryl derivatives of tin, silicon, boron and the like, such as phenylboronic acid). A phenylboronic acid may be prepared by treating an aryl halide with n-butyllithium or magnesium turnings in an anhydrous organic solvent (e.g., tetrahydrofuran) and adding trimethylborate and finally aqueous hydrochloric acid.

For compounds wherein any of $R^1$ to $R^5$ or $R^{12}$ comprise reactive functionalities, the reactants may be treated with protecting agents prior to coupling. Suitable protecting agents and procedures for use thereof are generally known in the art. Exemplary protecting groups are benzyl, halocarbobenzyloxy, tosyl and the like for hydroxyl; and carbobenzyloxy, halocarbobenzyloxy, acetyl, benzoyl and the like for amino. Such groups may then be removed from the resulting protected analogue of compound I by treatment with one or more deprotecting agents. Suitable deprotecting agents and procedures for use thereof are generally known in the art.

Similarly, the nitrogen atom of the sulfonamide core may need to be protected during preparation of compound I. Suitable protecting groups are also generally known in the art. The protecting group may be added by treating the free amine with the halide of the protecting group at about 0° C. in the presence of a base (e. g., triethylamine). The protecting group may be removed by treatment with an acid (e. g., trifluoroacetic acid) in an organic solvent (e. g., methylene chloride) at about 0° C.

The invention will now be further described by the following working examples, which are preferred embodiments of the invention. These examples are meant to be illustrative rather than limiting.

EXAMPLE 1

N-(6-Chloro-3-pyridazinyl)-5-(dimethylamino)-1-naphthalenesulfonamide

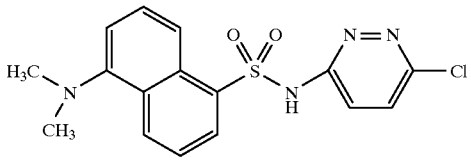

A solution of dansylamide (0.50 g, 2.00 mmol), 3,6-dichloropyridazine (0.37 g, 2.50 mmol) and cesium carbonate (1.33 g, 4.10 mmol) in dimethylformamide (2 mL) was heated at 105° C. for 6 hours, allowed to cool, and poured into water. The solution was acidified to pH 3 and the resulting brown solid was filtered and washed with water. The solid was dissolved in half saturated aqueous sodium bicarbonate. The solution was acidified to pH 3 and the resulting brown solid was filtered, washed with water and dissolved in 10% isopropanol/methylene chloride. The solution was washed with brine, dried (magnesium sulfate) and evaporated. The residue was chromatographed on silica with 2%, then 3% methanol/methylene chloride to afford 0.29 g of product containing a small amount of dansylamide. The solid was dissolved in half saturated aqueous sodium bicarbonate and the solution was filtered. The filtrate was acidified to pH 3 with solid potassium hydrogen sulfate and extracted with methylene chloride. The organic solution was dried (magnesium sulfate) and evaporated to afford 0.24 g (33%) of Example 1 as a bright yellow solid. Melting point: 92–100° C.

Analysis calculated for $C_{16}H_{15}N_4O_2SCl \cdot 0.41\ H_2O \cdot 0.15\ C_4H_{10}O$. Calc'd: C, 52.29; H, 4.58; N, 14.69; S, 8.40; Cl, 9.30. Found: C, 52.29; H, 4.34; N, 14.53; S, 8.32; Cl, 9.38.

EXAMPLE 2

N-(6-Chloro-5-methyl-3-pyridazinyl)-5-(dimethylamino)-1-naphthalenesulfonamide

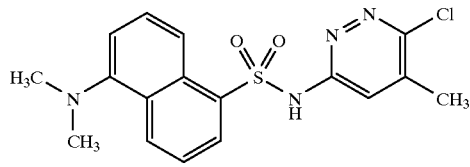

A solution of dansylamide (1.5 g, 6.0 mmol), 3,6-dichloro-4-methylpyridazine (0.98 g, 6.0 mmol) and cesium carbonate (4.1 g, 12.6 mmol) in dimethylformamide (8 mL) was heated at 105° C. for 8 hours, allowed to cool, and poured into half-saturated sodium hydrogen carbonate (300 mL). A large amount of a black gummy solid was filtered from the solution, and the filtrate was acidified with solid potassium hydrogen sulfate and extracted with methylene chloride (3x). The combined organic phases were dried (magnesium sulfate), evaporated and warmed under high vacuum to afford 1.03 g of black gum. Flash chromatography on silica (30%, then 50% ethyl acetate/hexanes) afforded 0.17 g of crude faster moving isomer (FMI; TLC, 50% ethyl acetate/hexanes, $R_f$=0.60) as a pink solid and 0.19 g of nearly clean slower moving isomer (SMI; TLC, 50% ethyl acetate/hexanes, $R_f$=0.43) as a grey green gum. The SMI material was recrystallized from ethyl acetate/hexanes to afford 93 mg (4%) of Example 2 as an off white solid. Melting point: 112–115° C.

Analysis calculated for $C_{17}H_{17}N_4O_2SCl$-0.07 $H_2O$. Calc'd: C, 53.99; H, 4.57; N, 14.81; S, 8.48; Cl, 9.37. Found: C, 53.99; H, 4.36; N, 14.84; S, 8.36; Cl, 9.35.

EXAMPLE 3

N-(6-Chloro-4-methyl-3-pyridazinyl)-5-(dimethylamino)-1-naphthalenesulfonamide

The FMI material from Example 2 was suspended in 5% aqueous sodium hydrogen carbonate, methanol was added, and the solution was warmed until nearly complete dissolution took place. The solution was evaporated to remove only the methanol and the resulting heterogeneous solution was filtered of insoluble dansylamide. The filtrate was acidified with solid potassium hydrogen sulfate and extracted with ethyl acetate. The organic phase was dried (magnesium sulfate) and evaporated to afford 130 mg of pink solid, which was dissolved in a small amount of warm ethyl acetate. Hexane was added and the product was allowed to crystallize. The crystalline solid was filtered, rinsed with ethyl acetate/hexanes and dried to afford 96 mg (4%) of Example 3 as a yellow solid. Melting point: 192–194° C.

Analysis calculated for $C_{17}H_{17}N_4O_2SCl$. Calc'd: C, 54.18; H, 4.55; N, 14.87; S, 8.51; Cl, 9.41. Found: C, 54.25; H, 4.56; N, 14.69; S, 8.22; Cl, 9.40.

EXAMPLE 4

N-(6-Chloro-3-pyridazinyl)[1,1'-biphenyl]-2-yl-sulfonamide

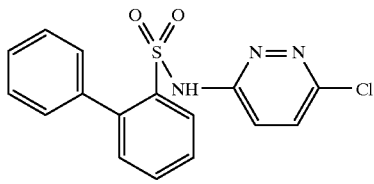

A. [1,1'-biphenyl]-2-yl-sulfonamide

To a degassed solution of 2-bromo-benzenesulfonamide (0.7 g, 3.0 mmole) and tetrakis(triphenylphosphine) palladium (0) (0.21 g, 0.18 mmole) in benzene (25 mL) was added 2M aqueous sodium carbonate (15 mL) followed by a solution of phenylboronic acid (0.44 g, 3.6 mmole) in 95% aqueous ethanol. The two phase solution was refluxed for 18 hours, cooled to room temperature and diluted with water. The mixture was extracted twice with ethyl acetate and the combined organic phases were washed with brine, dried (magnesium sulfate) filtered and evaporated. The residue was chromatographed (silica get, 2:1 hexanes:ethyl acetate) to afford 0.25 g (36%) of compound A as a yellow solid.

B. N-(6-Chloro-3-pyridazinyl)[1,1'-biphenyl]-2-yl-sulfonamide

To a solution of compound A (0.30 g, 1.3 mmol) and 3,6-dichloropyridazine (0.21 g, 1.4 mmol) in dry dimethylformamide (4 mL) was added cesium carbonate (0.46 g, 1.4 mmol). The mixture was heated at 105° C. for 24 hours, cooled to room temperature, diluted with water (40 mL) and acidified to pH 4 with 6N aqueous hydrochloric acid. The resulting tan precipitate was collected by filtration, rinsed with water and dissolved in ethyl acetate. The solution was extracted 3 times with 2N aqueous sodium carbonate (3×50 mL) and the combined extracts were acidified to pH 4 with 6N aqueous hydrochloric acid. The resulting tan precipitate was collected by filtration, rinsed with water, and dried under vacuum to afford 0.24 g (54%) of Example 4 as a tan solid, m.p. 176–181° C.

Analysis calculated for $C_{16}H_{12}N_3O_2SCl$-1.11 $H_2O$. Calc'd: C, 52.53; H, 3.92; N, 11.49; S, 8.76; Cl, 9.68. Found: C, 52.78; H, 3.69; N, 11.24; S, 8.70; Cl, 9.39.

EXAMPLE 5

N-(6-Chloro-3-pyridazinyl)-4'-(2-methylpropyl)[1,1'-biphenyl]-2-sulfonamide

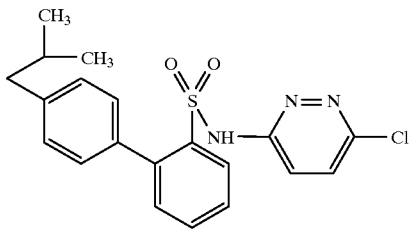

A. 4-(2-methylpropyl)-benzeneboronic acid

To a suspension of 0.68 g (28.15 mmol) of magnesium turnings in 50 mL of tetrahydrofuran under argon, a crystal of iodine was added and a solution of 4-bromoisobutylbenzene (6.0 g, 28.15 mmol) in 25 mL of tetrahydrofuran was added at such a rate that a gentle reflux was maintained. The mixture was refluxed for an additional hour, cooled to room temperature and added in portions over 15 minutes to a solution of trimethylborate (2.93 g, 28.15 mmol) in 50 mL of ether at −78° C. under argon. After 30 minutes at −78° C., the solution was warmed to room temperature, stirred for 90 minutes and 10% aqueous hydrochloric acid (100 mL) was added. After 10 minutes, the solution was extracted with ether (3×100 mL) and the combined ether extracts were extracted with 1 M sodium hydroxide (3×100 mL). The aqueous extracts were acidified with dilute hydrochloric acid to pH 2 and extracted with ether (3×100 mL). The combined ether extracts were washed once with water (100 mL), dried and evaporated to afford 3.5 g of a white solid. Crystallization from ether/hexanes provided 2.3 g (46%) of compound A as a white solid in two crops, m.p. 134–135° C.

B. N-(1,1-dimethylethyl)-4'-(2-methylpropyl)-1,1'-biphenyl-2-sulfonamide

To a solution of N-(1,1-dimethylethyl)-2-bromobenzenesulfonamide (500 mg, 1.71 mmol) in toluene (14 mL), sodium carbonate (363 mg, 3.42 mmol) in water (7 mL) and compound A (366 mg, 2.05 mmol) in ethanol (7 mL) (all solvents argon-degassed) was added tetrakis (triphenylphosphine)palladium (0) (119 mg, 0.103 mmol). The yellow mixture was heated at reflux for 1 hour, cooled to room temperature and poured into half-saturated sodium bicarbonate (30 mL). The mixture was extracted with ethyl acetate (2×50 mL) and the combined organic layers were dried (magnesium sulfate) and evaporated. Chromatography (silica, 10% ethyl acetate/hexanes) afforded compound B as a white solid (503 mg, 85%).

C. 4'-(2-methylpropyl)-1,1'-biphenyl-2-sulfonamide

A solution of compound B (503 mg, 1.45 mmol) in cold trifluoroacetic acid (5 mL) was stirred for 5 hours as it warmed to room temperature. The solvent was evaporated and the residue was passed through a silica plug with ethyl acetate. The eluate was evaporated to provide compound C as an oil (306 mg, 100%).

D. N-(6-Chloro-3-pyridazinyl)-4'-(2-methylpropyl)[1,1'-biphenyl]-2-sulfonamide

To a solution of compound C (300 mg, 1.73 mmol) and 3,6-dichloropyridazine (350 mg, 2.34 mmol) in dry dimethylformamide (4 mL) was added cesium carbonate (770 mg, 2.34 mmol). The mixture was heated at 100° C. for 3 hours, cooled to room temperature, diluted with water (75 mL) and acidified to pH 3 with 6N aqueous hydrochloric acid. The mixture was extracted with ethyl acetate (3×50 mL) and the combined organic phases were washed with water and brine, and dried (magnesium sulfate). The residue was chromatographed on silica gel using 2:3 ethyl acetate/hexanes to afford 200 mg (29%) of Example 5 as a tan solid, mp 108–110° C.

Analysis for $C_{20}H_{20}N_3O_2SCl\cdot0.15\ H_2O$. Calc'd: C, 59.37; H, 5.05; N, 10.38; S, 7.92; Cl, 8.76. Found: C, 59.37; H, 4.99; N, 10.03; S, 7.94; Cl, 9.09.

What is claimed is:

1. A compound of the formula

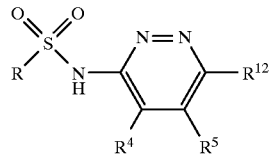

or a pharmaceutically acceptable salt thereof, wherein:

R is naphthyl or biphenyl, each of which may be substituted with $R^1$, $R^2$ and $R^3$;

$R^1$, $R^2$ and $R^3$ are each independently
  (a) hydrogen;
  (b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$;
  (c) halo;
  (d) hydroxyl;
  (e) cyano;
  (f) nitro;
  (g) —C(O)H or —C(O)$R^6$;
  (h) —CO$_2$H or —CO$_2R^6$;
  (i) —SH, —S(O)$_n R^6$, —S(C)$_m$—OH, —S(O)$_m$—O$R^6$, —O—S(O)$_m$—$R^6$, —OS(O)$_m$OH or —O—S(O)$_m$—O$R^6$;
  (j) —$Z^4$—N$R^7R^8$; or
  (k) —$Z^4$—N($R^{11}$)—$Z^5$—N$R^9R^{10}$;

$R^4$, $R^5$ and $R^{12}$ are each independently
  (a) hydrogen;
  (b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$;
  (c) halo;
  (d) hydroxyl;
  (e) cyano;
  (f) nitro;
  (g) —C(O)H or —C(O)$R^6$;
  (h) —CO$_2$H or —CO$_2R^6$;
  (i) —SH, —S(O)$_n R^6$, —S(O)$_m$—OH, —S(O)$_m$—O$R^6$, —O—S(O)$_m$—$R^6$, —O—S(O)$_m$OH or —O—S(O)$_m$—O$R^6$;
  (j) —$Z^4$—N$R^7R^8$; or
  (k) —$Z^4$—N($R^{11}$)—$Z^5$—N$R^9R^{10}$;

$R^6$ is alkyl, alkenyl, alkynyl, alkoxy, cycloalkyl, cycloalkylalkyl, cycloalkenyl, cycloalkenylalkyl, aryl or aralkyl, any of which may be substituted with $Z^1$, $Z^2$ and $Z^3$;

$R^7$ is
  (a) hydrogen;
  (b) alkyl, alkenyl, alkynyl, alkoxy, cycloalkyl, cycloalkylalkyl, cycloalkenyl, cycloalkenylalkyl, aryl or aralkyl, any of which may be substituted with $Z^1$, $Z^2$ and $Z^3$;
  (c) cyano;
  (d) hydroxyl;
  (e) —C(O)H or —C(O)$R^6$;
  (f) —CO$_2R^6$; or
  (g) —SH, —S(O)$_n R^6$, —S(O)$_m$—O$R^6$, —O—S(O)$_m$—$R^6$ or —O—S(O)$_m$—O$R^6$, except in the group —$Z^4$—N$R^7R^8$ when $Z^4$ is —S(O)$_n$—;

$R^8$ is
  (a) hydrogen;
  (b) —C(O)H or —C(O)$R^6$, except in the group —$Z^4$—N$R^7R^8$ when $Z^4$ is —C(O)— and $R^7$ is —C(O)H, —C(O)$R^6$ or —CO$_2R^6$; or
  (c) alkyl, alkenyl, alkynyl, alkoxy, cycloalkyl, cycloalkylalkyl, cycloalkenyl, cycloalkenylalkyl, aryl or aralkyl, any of which may be substituted with $Z^1$, $Z^2$ and $Z^3$;

$R^9$ is
  (a) hydrogen;
  (b) hydroxyl;
  (c) —C(O)H or —C(O)$R^6$;
  (d) —CO$_2R^6$;
  (e) —SH, —S(O)$_n R^6$, —S(O)$_m$—O$R^6$, —O—S(O)$_m$—$R^6$ or —O—S(O)$_m$—O$R^6$; or
  (f) alkyl, alkenyl, alkynyl, alkoxy, cycloalkyl, cycloalkylalkyl, cycloalkenyl, cycloalkenylalkyl, aryl or aralkyl, any of which may be substituted with $Z^1$, $Z^2$ and $Z^3$;

$R^{10}$ is
  (a) hydrogen;
  (b) —C(O)H or —C(O)$R^6$, except when $Z^5$ is —C(O)— and $R^9$ is —C(O)H, —C(O)$R^6$ or —CO$_2R^6$; or
  (c) alkyl, alkenyl, alkynyl, alkoxy, cycloalkyl, cycloalkylalkyl, cycloalkenyl, cycloalkenylalkyl, aryl or aralkyl, any of which may be substituted with $Z^1$, $Z^2$ and $Z^3$;

$R^{11}$ is
  (a) hydrogen;
  (b) hydroxyl or —CO$_2R^6$, except when one of $R^9$ and $R^{10}$ is hydroxyl or —CO$_2R^6$;
  (c) —C(O)H or —C(O)$R^6$; or
  (d) alkyl, alkenyl, alkynyl, alkoxy, cycloalkyl, cycloalkylalkyl, cycloalkenyl, cycloalkenylalkyl, aryl or aralkyl, any of which may be substituted with $Z^1$, $Z^2$ and $Z^3$;

$Z^1$, $Z^2$ and $Z^3$ are each independently (a) hydrogen;
(b) halo;
(c) hydroxy;
(d) alkyl, alkenyl, aralkyl, alkoxy, aryloxy or aralkoxy;
(e) —SH, —S(O)$_n$Z$^6$, —S(O)$_m$—OH, —S(O)$_m$—OZ$^6$, —O—S(O)$_m$—Z$^6$, —O—S(O)$_m$OH or —O—S(O)$_m$—OZ$^6$;
(f) oxo;
(g) nitro;
(h) cyano;
(i) —C(O)H or —C(O)Z$^6$;
(j) —CO$_2$H or —CO$_2$Z$^6$; or
(k) —Z$^4$—NZ$^7$Z$^8$, —Z$^4$—N(Z$^{11}$)—Z$^5$Z$^6$ or —Z$^4$—N(Z$^{11}$)—Z$^5$—NZ$^7$Z$^8$;

Z$^4$ and Z$^5$ are each independently
(a) a single bond;
(b) —Z$^9$—S(O) m—Z$^{10}$;
(c) —Z$^9$—C(O)—Z$^{10}$;
(d) —Z$^9$—C(S)—Z$^{10}$;
(e) —Z$^9$—O—Z$^{10}$;
(f) —Z$^9$—S—Z$^{10}$;
(g) —Z$^9$—O—C(O)—Z$^{10}$; or
(h) alkyl, alkenyl, alkynyl, cycloalkyl, cycloalkylalkyl, cycloalkenyl, cycloalkenylalkyl, aryl or aralkyl, any of which may be substituted with Z$^1$, Z$^2$ and Z$^3$;

Z$^6$, Z$^7$ and Z$^8$ are each independently hydrogen, alkyl, alkenyl, alkynyl, cycloalkyl, cycloalkylalkyl, cycloalkenyl, cycloalkenylalkyl, aryl, or aralkyl;

Z$^9$ and Z$^{10}$ are each independently a single bond, alkylene, alkenylene or alkynylene;

Z$^{11}$ is
(a) hydrogen;
(b) hydroxyl;
(c) —C(O)H, —C(O)Z$^6$ or —CO$_2$Z$^6$, provided that when Z$^{11}$ is —CO$_2$Z$^6$, Z$^6$ is other than hydrogen; or
(d) alkyl, alkenyl, alkynyl, alkoxy, cycloalkyl, cycloalkylalkyl, cycloalkenyl, cycloalkenylalkyl, aryl or aralkyl;

m is 1 or 2; and
n is 0, 1 or 2.

2. The compound of claim 1, wherein R is

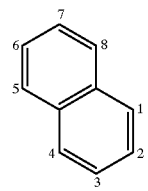

with the sulfonamide attached at position 1 or 2 and one of R$^1$, R$^2$ and R$^3$ attached at position 5 or 6.

3. The compound of claim 2, wherein one of R$^1$, R$^2$ and R$^3$ is —NR$^7$R$^8$.

4. The compound of claim 3, wherein R$^7$ and R$^8$ are each independently hydrogen, alkyl or C(O)alkyl.

5. The compound of claim 4, wherein R$^7$ and R$^8$ are each independently hydrogen, methyl, methylethyl or acetyl.

6. The compound of claim 2, wherein R$^4$, R$^5$ and R$^{12}$ are independently hydrogen, alkyl or halo.

7. The compound of claim 1, having the formula

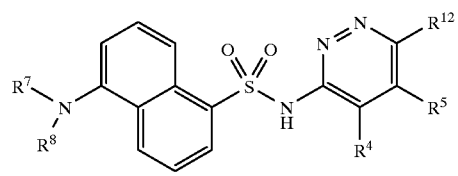

8. The compound of claim 7, wherein R$^7$ and R$^8$ are each independently hydrogen, alkyl or C(O)alkyl.

9. The compound of claim 8, wherein R$^7$ and R$^8$ are each independently hydrogen, methyl, methylethyl or acetyl.

10. The compound of claim 1, wherein R is biphenyl which may be substituted with R$^1$, R$^2$ and R$^3$.

11. The compound of claim 10, wherein one of R$^1$, R$^2$ and R$^3$ is 4'-alkyl or 4'-branched alkyl.

12. The compound of claim 11, wherein one of R$^1$, R$^2$ and R$^3$ is 4'-alkyl.

13. The compound of claim 11, wherein one of R$^1$, R$^2$ and R$^3$ is 4'-branched alkyl.

14. The compound of claim 1, selected from the group consisting of:

N-(6-Chloro-3-pyridazinyl)-5-(dimethylamino)-1-naphthalenesulfonamide;

N-(6-Chloro-5-methyl-3-pyridazinyl)-5-(dimethylamino)-1-naphthalenesulfonamide;

N-(6-Chloro-4-methyl-3-pyridazinyl)-5-(dimethylamino)-1-naphthalenesulfonamide;

N-(6-Chloro-3-pyridazinyl)[1,1'-biphenyl]-2-yl-sulfonamide; and

N-(6-Chloro-3-pyridazinyl)-4'-(2-methylpropyl)[1,1'-biphenyl]-2-sulfonamide.

* * * * *